United States Patent [19]
Andoh et al.

[11] Patent Number: 4,521,622
[45] Date of Patent: Jun. 4, 1985

[54] PROCESS FOR PRODUCING AROMATIC AMINE

[75] Inventors: Naoki Andoh; Shuetsu Fujiwara, both of Yokohama, Japan

[73] Assignee: Japan Synthetic Rubber Co., Ltd., Tokyo, Japan

[21] Appl. No.: 576,956

[22] Filed: Feb. 3, 1984

[30] Foreign Application Priority Data

Feb. 15, 1983 [JP] Japan .................................. 58-22052
Aug. 24, 1983 [JP] Japan ................................ 58-154418
Oct. 31, 1983 [JP] Japan ................................ 58-202771

[51] Int. Cl.$^3$ ............................................. C07C 85/04
[52] U.S. Cl. ..................................... 564/406; 564/407
[58] Field of Search ................................ 564/406, 407

[56] References Cited

U.S. PATENT DOCUMENTS 1,726,170  8/1929  Britton et al. ....................... 564/407
1,726,172  8/1929  Williams et al. .................... 564/407
1,764,869  6/1930  Hale .................................... 564/407
1,994,845  3/1935  Wuertz ................................ 564/406
4,380,670  4/1983  Nishiyama et al. ................. 564/407
4,421,694  12/1983 Krüger et al. ................. 564/406 X
4,443,630  4/1984  Papenfuhs et al. ................. 564/406

Primary Examiner—Paul F. Shaver
Attorney, Agent, or Firm—Oblon, Fisher, Spivak, McClelland & Maier

[57] ABSTRACT

A process for producing an aromatic amine from an aromatic halide and ammonia, characterized by comprising the following steps (1), (2) and (3):

step (1): reacting the aromatic halide with ammonia in the presence of water by using a catalyst comprising a copper compound as the main constituent, step (2): extracting the aromatic amine from the reaction mixture obtained in step (1) without depositing or separating the copper component contained in the reaction mixture, and step (3): adding an alkali metal hydroxide and/or an alkaline earth metal hydroxide to the raffinate aqueous solution obtained by the extraction procedure in step (2) to deposit copper compounds and separating the same.

This process is good in reaction efficiency and permits easy recovery of the catalyst. In the process described above, the extraction of the desired product can be made more effective by incorporating, before step (2), a step of adding to the reaction mixture obtained in step (1) an alkali metal hydroxide and/or an alkaline earth metal hydroxide in an amount of 0.05 to 1 gram equivalent per gram ion of halogen ions contained in said mixture.

14 Claims, 1 Drawing Figure

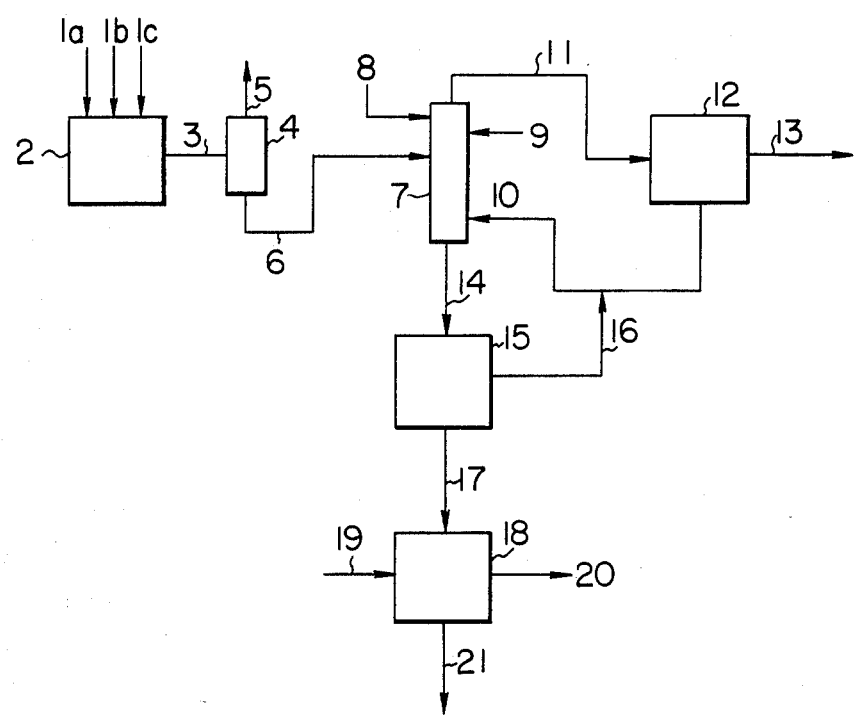

PROCESS FOR PRODUCING AROMATIC AMINE

This invention relates to a process for producing an aromatic amine and aims at providing an excellent process for producing an aromatic amine which process is good in reaction efficiency and permits easy recovery of a catalyst.

As a process for producing an aromatic amine, a process has heretofore been known by which at least one aromatic halide is reacted with ammonia in the presence of water using a copper compound as a catalyst.

However, this process is disadvantageous particularly in separation of the copper component of catalyst after the reaction.

In Japanese Patent Publication Nos. 33,707/80, 33/708/80 and 33,709/80, there are proposed methods which can solve the problem of separation of the copper compound catalyst and enable the recovered copper compound to be re-used as the catalyst. These methods comprise first adding an alkali metal hydroxide to the reaction mixture to deposit the copper component of catalyst in the form of a copper oxide, and separating the same, and then separating the objective substance by distillation or extraction. The copper oxide recovered by this method is effective as the catalyst and can be reused. However, these methods are disadvantageous in that the copper oxide deposited is colloidal, so that the separation thereof is very difficult. Moreover, a fairly large amount of copper ions which do not form a precipitate remain in the reaction mixture. Therefore, there is the problem that a treatment step is required for removing the copper ions in the disposal treatment of the residue after the separation of the objective substance following the precipitation of the copper oxide.

Japanese patent application Kokai (Laid-Open) No. 59,824/76 proposes a method in which instead of the precipitation of the copper components of the catalyst followed by its separation, a part of the ammonium chloride which is a by-product existing in the raffinate aqueous solution is crystallized out and then separated, and the resulting residue containing the catalyst is re-used as it is. However, this method is disadvantageous in that since the residue to be reused contains a large amount of ammonium chloride, the rate of the intended reaction is lowered and the selectivity is also reduced. Furthermore, since a considerable amount of the copper component is contained in the ammonium chloride separated and it is difficult to completely remove the copper component even by such a procedure as recrystallization or the like. Therefore, the ammonium chloride obtained cannot be used as fertilizers and the like and the disposal treatment of the ammonium chloride is not easy.

As described above, the process for producing an aromatic amine from an aromatic halide and ammonia have the above-mentioned various disadvantages, in spite of the fact that the raw materials are easily available and the objective substance can be obtained by a small number of steps. Accordingly, said processes have not yet been industrialized.

This invention has been made under such circumstances and aims at providing an efficient process for producing an aromatic amine which is good in reaction efficiency, permits easy recovery of a catalyst and is free from the problem of treatment of wastes.

According to this invention, there is provided a process for producing an aromatic amine from an aromatic halide and ammonia, characterized by comprising the following steps (1), (2) and (3):

step (1): reacting an aromatic halide with ammonia in the presence of water using a catalyst comprising a copper compound as the main constituent, step (2): extracting the aromatic amine from the reaction mixture obtained in step (1) without depositing or separating the copper component contained in the reaction mixture, and step (3): adding an alkali metal hydroxide and/or an alkaline earth metal hydroxide to the raffinate aqueous solution obtained by extraction procedure in step (2) to deposit the copper compounds, and separating the same.

In this invention, the aromatic halide is first reacted with ammonia in the presence of water using a catalyst comprising a copper compound as the main constituent (reaction step).

The aromatic halide includes, for example, chlorobenzene, dichlorobenzene, trichlorobenzene, chloroaniline, dichloroaniline, chloronitrobenzene, dichloronitrobenzene and the like, and preferable are chlorobenzene, dichlorobenzene, chloroaniline and trichlorobenzene. The above aromatic halides may be used alone or in admixture of two or more.

The amount of the ammonia used is preferably 2 to 25 moles, more preferably 4 to 20 moles, per gram-atom of the halogen of the aromatic halide which requires amination.

The amount of the water used is preferably 30 to 70% by weight, more preferably 45 to 65% by weight, based on the total weight of the ammonia and the water.

The amount of the copper compound used is preferably 0.01 to 0.4 gram-atom, more preferably 0.02 to 0.2 gram-atom, in terms of copper atom per mole of the aromatic halide. The copper compound used as a catalyst includes copper oxides, copper hydroxides, copper halides, and the like. In particular, cuprous oxide, cupric oxide, cupric hydroxide, cuprous halides and cupric halides are preferred, and mixed hydroxides, mixed oxides or mixed halides of copper and alkaline earth metals can be used as preferable catalysts.

When an alkaline earth metal such as calcium or the like is contained in the copper compound, the content is preferably 10 gram-atoms, more preferably 0.1 to 5 gram-atoms, per gram-atom of the copper.

The temperature for the reaction of the aromatic halide and ammonia in this invention is preferably 170° C. to 250° C., more preferably 200° to 240° C., and the reaction time is usually 2 to 40 hours. When the reaction is continuously effected, it is preferable to connect two or more reactors with one another in series, and the residence time of the reaction solution in the reactors is adjusted so as to be the desired reaction time.

The aromatic amine which can be thus produced includes chloroaniline, phenylenediamine, chlorophenylenediamine, triaminobenzene, and the like.

After completion of the reaction, the reaction mixture obtained is cooled to preferably 20° to 80° C., more preferably 30° to 70° C., and if necessary, the pressure in the reaction system is returned to atmospheric pressure, whereby ammonia in the reaction mixture is removed in the form of a gas, so that the pressure in the subsequent steps can be reduced. However, ammonia in the reaction mixture at atmospheric pressure need not be removed.

Subsequently, the aromatic amine, i.e., the objective substance, and the residual materials or intermediates such as chloroaniline, aniline, dichlorobenzene and the like are extracted from the reaction mixture with an extracting solvent comprising as the main constituent an alcohol whose main chain has 3 to 6 carbon atoms such as propanol, butanol, pentanol, hexanol or the like; aniline; an aniline derivative; tetrahydrofuran; or the like (extraction step). The extracting solvent in this extraction step is preferably tetrahydrofuran from the viewpoint of the distribution ratio of the aromatic amine to the extracting solvent, and in view of the fact that the purified aromatic amine, particularly phenylenediamine, recovered from the extract by distillation or the like is excellent in storage stability. An organic solvent, for example, dipropyl ether, dibutyl ether or the like may be added to the extracting solvent in an amount of about 30% by weight or less based on the weight of the extracting solvent.

In extracting the aromatic amine and the like from the reaction mixture, it is possible to add, to the reaction mixture obtained, an alkali metal hydroxide and/or an alkaline earth metal hydroxide in an amount of 0.05 to 1 gram-equivalent per gram-ion of halogen ions contained in said reaction mixture prior to the extraction, in order to facilitate the extraction operation in the above-mentioned extraction step and improve the distribution ratio of the aromatic amine to the extracting solvent. The term "distribution ratio" used herein is defined by the following equation:

$$\text{Distribution ratio} = \frac{\text{Aromatic amine concentration in extract (\% by weight)}}{\text{Aromatic amine concentration in raffinate aqueous solution (\% by weight)}}$$

Although the reason why the distribution ratio of the aromatic amine to the extracting solvent is improved by the addition of an alkali metal hydroxide and/or an alkaline earth metal hydroxide is not clear, it is presumed that the ammonium halide produced as by-product in the reaction step reacts with the alkali metal hydroxide and/or the alkaline earth metal hydroxide, so that the ammonium halide content of the reaction mixture decreases, resulting in a reduction of the solubility of the aromatic amine in the aqueous layer of the reaction mixture.

When the amount of the alkali metal hydroxide and/or the alkaline earth metal hydroxide added to the reaction mixture is less than 0.05 gram-equivalent per gram-ion of the halogen ions, the enhancement of distribution ratio of the aromatic amine is not sufficient. On the other hand, when it exceeds 1 gram-equivalent, the copper component in the reaction mixture begins to deposit as in the catalyst separation step described hereinafter and the resulting precipitate hinders smooth operation in the subsequent extraction step, and moreover, under some conditions for extraction operation in the extraction step, the alkali metal halide and/or alkaline earth metal halide produced as by-product deposits and the resulting precipitate blocks the extractor.

The alkali metal hydroxide and the alkaline earth metal hydroxide include, for example, sodium hydroxide, potassium hydroxide, calcium hydroxide and magnesium hydroxide. The alkali metal hydroxide and/or alkaline earth metal hydroxide is usually added in the form of an aqueous solution or suspension having a concentration of about 5 to about 60% by weight, and is allowed to react with the reaction mixture preferably at 30° to 80° C.

Since this operation causes a decrease of the solubility of ammonia in the reaction mixture, so that the pressure in the system is increased, it is also possible, if necessary, to decrease the pressure in the system again by carrying out gas-liquid separation to release the ammonia gas.

It is also possible to carry out simultaneously both the step of adding the alkali metal hydroxide and/or the alkaline earth metal hydroxide and the step of removing the ammonia gas by gas-liquid separation.

From the extract obtained in the extraction step, the extracting solvent and the objective aromatic amine are separated by a means such as distillation, crystallization or the like and recovered. When the extract is treated by distillation, crystallization or the like, the ammonium halide dissolved in a small amount in the extract causes troubles in this step in some cases. For example, when it is intended to recover the extracting solvent from the extract by distillation, the ammonium halide decomposes upon heating and the decomposition products react with the coexisting aromatic amine to give nonvolatile heavy materials, which adhere, upon heating, to the inner wall of the distillation apparatus and solidifies, so that the distillation apparatus tends to be blocked therewith.

Although the amount of the ammonium halide contained in the extract varies depending on the kind of the extracting solvent, it cannot be reduced to zero since a hydrophilic extracting solvent is used.

Therefore, it is preferable to reduce the amount of the ammonium halide in the extract to a great extent or to substantially zero by washing the extract obtained in the extraction step with an aqueous alkali metal hydroxide solution (for example, about 1 to 50% by weight) (hereinafter referred to as "the alkali washing"), by washing said extract with an aqueous alkali metal halide solution (for example, from 3% by weight to saturation point) (hereinafter referred to as "the salt washing"), or by combination of the two kinds of washing, before the separation of the aromatic amine from the extract by distillation or the like. When some extracting solvents are used, the extract may be washed with water.

In the case of the alkali washing, the ammonium halide in the extract is converted into an alkali metal halide, which causes much less the abovementioned troubles in the distillation step than does the ammonium halide. Also in the case of the salt washing, the ammonium halide concentration in the extract can be made very low (about 0.01 to 0.2% by weight).

A specific example of the alkali washing or the salt washing is shown below. For example, when the washing is carried out in a countercurrent liquid-liquid extraction column, the reaction mixture is fed to the middle of the column, the extracting solvent to the bottom of the column, the aqueous alkali metal halide solution to the top of the column, and the aqueous alkali metal hydroxide solution to the upper part of the column (a part between the top and the middle), and the feeding proportions of the reaction mixture, the extracting solvent, the aqueous alkali metal hydroxide solution and the aqueous alkali metal halide solution are adjusted to approximately 1:0.5–5:0.05–1:0.05–0.3. In this case, the alkali washing can serve also as the above-mentioned step of adding a small amount of an alkali metal hydroxide to the reaction mixture.

An alkali metal hydroxide and/or an alkaline earth metal hydroxide is added to the raffinate aqueous solution to deposit copper compounds comprising copper oxide and/or copper hydroxide as the main constituent, and then separate them (catalyst separation step).

The raffinate aqueous solution contains, besides copper ions, ammonium halide, alkali metal halide and/or alkaline earth metal halide, ammonia and the dissolved extracting solvent, and further contains the aromatic amine remaining unextracted and the unreacted materials in a small amount. Therefore, if necessary, the extracting solvent, the aromatic amine, the unreacted materials and the like are removed by azeotropic distillation, steam distillation or the like. Thereafter, an alkali metal hydroxide such as sodium hydroxide, potassium hydroxide or the like and/or an alkaline earth metal hydroxide such as magnesium hydroxide, calcium hydroxide or the like, preferably an alkali metal hydroxide, is added to said raffinate aqueous solution with sufficient stirring, whereby the copper ions in the residual aqueous solution after the extraction is deposited in the form of copper compounds comprising copper oxide and/or copper hydroxide as the main constituents.

In the step of depositing the copper compounds, when an alkali metal hydroxide is used alone or when an alkali metal hydroxide and an alkaline earth metal hydroxide are simultaneously used, sufficient stirring is conducted after the addition of these compounds, and the resulting solution is thereafter made basic, preferably pH 10 or more, more preferably pH 12 or more. The temperature is preferably adjusted to 50° C. or more, more preferably boiling point, whereby most of the copper compounds are deposited in the form of copper oxides and, at the same time, the ammonium halide contained in the solution decomposes to release ammonia.

The copper compounds deposited are separated by filtration or the like and recovered. The copper compounds recovered have a substantially the same catalytic activity as the copper oxides, copper hydroxides and copper halides, and can as such be reused as the catalyst.

When an alkaline earth metal hydroxide is mainly used in the step of depositing the copper compounds, it is added preferably in an amount of 1 mole-equivalent per gram-ion of ammonium ions in the raffinate aqueous solution, and the pH of the resulting mixture is adjusted to preferably 5.5 to 9.5, more preferably 6.0 to 7.0. In this case, merely heating and stirring cause an insufficient deposition of the copper compounds in some cases. In such cases, the ammonia in the raffinate aqueous solution is removed by distillation or by blowing a non-reactive, non-condensable gas such as air, nitrogen or the like into the solution or by distillation, thereby accelerating the deposition of the copper compounds. In this case, the copper compounds are precipitated along with the alkaline earth metal hydroxide, and therefore, it is impossible to obtain copper compounds of high purity. However, as a catalyst, the copper compounds may contain the alkaline earth metal, and in some cases, the reaction rate is increased by reuse of the recovered copper compounds as a catalyst so long as care is taken to keep the alkaline earth metal content in a preferable range.

Even when an alkali metal hydroxide is used alone or even when an alkali metal hydroxide and an alkaline earth metal hydroxide are used together, the non-condensable gas may be blown into the solution in order to accelerate the deposition of the copper compounds.

The filtrate obtained by separating the copper compounds deposited contains only an extremely slight amount of copper ions, and hence can easily be treated by a conventional waste water treatment such as active sludge treatment, active carbon treatment or the like.

This invention is more specifically explained below referring to the accompanying drawing, which shows a flow sheet of the production of an aromatic amine which is an embodiment of this invention.

In the drawing, the starting materials are fed through an aromatic halide feeding pipe 1a, an ammonia feeding pipe 1b and a-catalyst-water feeding pipe 1c and subjected to reaction in a reactor 2 to give a reaction mixture. The reaction mixture is introduced through a pipe 3 into a gas-liquid separator 4, where the excessive ammonia is discharged through a pipe 5, while the remaining reaction mixture is withdrawn through a pipe 6 and fed to a countercurrent liquid-liquid extraction column 7. An extracting solvent is fed through a pipe 10, an aqueous alkali metal hydroxide solution through a pipe 9 and an aqueous alkali metal halide solution through a pipe 8. The extract is sent through a pipe 11 to an extracting solvent separation step 12 (extraction step), and crude aromatic amine is discharged through a pipe 13. On the other hand, the raffinate aqueous solution is discharged through a pipe 14 and sent to an extracting solvent recovery step 15. In the step 15, the extracting solvent is recovered by distillation, and the recovered extracting solvent is returned through a pipe 16 to the pipe 10. The raffinate aqueous solution which has passed through the step 15 is sent through a pipe 17 to a catalyst recovery step 18. An alkali metal hydroxide and/or an alkaline earth metal hydroxide is fed through a pipe 19 to the step 18, and mixed with the raffinate aqueous solution, whereupon copper compounds are deposited. The copper compounds deposited are separated by filtration to obtain the recovered catalyst 20. Waste water is taken out through a pipe 21. The embodiment shown in the accompanying drawing illustrates one mode in which in an extraction column, the operation of adding a small amount of an alkali metal hydroxide to the reaction mixture, the extraction operation, the alkali washing and the salt washing are conducted simultaneously, and shows that the present invention involves not only the case where the individually steps are carried out separately, but also the case where they are rationalized into one step.

As described above, when an aromatic amine is produced according to this invention, the following effects can be obtained, and therefore, the process of this invention is suitable, in particular, for producing phenylenediamine.

(i) Since the copper compounds deposited in the separation and recovery of the catalyst comprising the copper compounds have a large particle diameter and a large apparent specific gravity, the procedure of separating them can be carried out smoothly and in a short time, and therefore, the present process is efficient.

(ii) The amount of the copper component remaining in the waste liquid can be made slight, so that the subsequent waste water treatment is easy.

(iii) Since the amounts of ammonium halide and the like contained in the extract can be reduced and moreover the amount of the extracting solvent used can be a relatively small, the present process is economical.

(iv) The step of adding a small amount of an alkali metal hydroxide and/or an alkaline earth metal hydroxide to the reaction mixture and the extraction step can greatly be simplified by modifying the extraction column type equipment and complicated equipment becomes unnecessary.

(v) Since the objective aromatic amine and the other aromatic compounds are separated before entering the step of recovering the copper compound catalyst, these useful substances are neither deteriorated nor lost by various operations such as alkali treatment and the like which are carried out in the subsequent step of recovering the catalyst. Therefore, the present process is advantageous.

This invention is explained below referring to Examples, but it should not be construed that the invention be restricted to the Examples.

EXAMPLE 1

Into a 1-liter, stainless steel autoclave equipped with an electromagnetic rotary stirrer were charged 150 g of o-dichlorobenzene, 375 g of 40% by weight aqueous ammonia and 7.0 g of cupric oxide, and they were heated to 220° C., and subjected to reaction for 12 hours. After the reaction, the autoclave was cooled to 60° C., and the valve was gradually opened while stirring the contents, to release the excessive ammonia gas. The internal pressure was lowered to atmospheric pressure, after which the reaction mixture in the autoclave was transferred to another vessel and stored. The conversion was 95%, and the selectivities were 79% for o-phenylenediamine, 14.5% for o-chloroaniline, and 3.7% for aniline. The above-mentioned reaction procedure was repeated 10 times, and all the reaction mixtures thus obtained were mixed together. Subsequently, by use of a vibration type countercurrent liquid-liquid extraction apparatus having an inside diameter of 15 mm and an effective height of 2.0 m, extraction was carried out using tetrahydrofuran in an amount of 1.5 kg per kg of the combined reaction mixture. The extraction percentage of o-phenylenediamine was 98%. Subsequently, the raffinate aqueous solution was transferred to a flask and distilled to remove the tetrahydrofuran.

Subsequently, 640 ml of a 25% by weight aqueous sodium hydroxide solution was dropped into the flask from the upper part of the flask while the contents were refluxed. At this time, ammonia gas was generated. The contents became a black suspension. The reflux was continued for another 15 minutes and the suspension was then allowed to stand, upon which copper compounds comprising black cupric oxide as the main constituent precipitated. A small amount of the transparent supernatant was taken out and the concentration of copper dissolved therein was measured. It was 50 ppm. The supernatant had a pH of 12.1. The flask was again heated, and air was blown into the contents for 1 hour under reflux. The flask was allowed to stand and the contents were filtered to recover the copper compounds comprising cupric oxide as the main constituent. The recovery was about 100% based on the calculated metallic copper content. The filtration was easy. A part of the filtrate was taken and the concentration of copper dissolved therein was measured to be 6 ppm.

The copper compounds recovered were again washed with distilled water and dried. When 7.0 g of the dried copper compounds were taken, and 150 g of o-dichlorobenzene and 375 g of 40% by weight aqueous ammonia were added thereto, after which the resulting mixture was subjected to reaction at 220° C. for 13 hours in the aforesaid autoclave, to obtain the following reaction results which were nearly equal to those obtained for the original cupric oxide: The conversion was 95.2%, and the selectivities were 79% for o-phenelenediamine, 14% for o-chloroaniline and 4% for aniline.

EXAMPLE 2

Into a 1-liter, stainless steel autoclave equipped with an electromagnetic rotary stirrer were charged 150 g of o-dichlorobenzene, 225 g of water, 150 g of ammonia and 15 g of cupric chloride dihydrate, and they were heated to 220° C., and subjected to reaction for 8 hours. After the reaction, the autoclave was cooled to 60° C., and the valve was gradually opened while stirring the contents, to release the excessive ammonia gas. The internal pressure was lowered to atmospheric pressure, after which the reaction mixture in the autoclave was transferred to another vessel and stored. The conversion was 97.5%, and the selectivities were 79.1% for o-phenylenediamine, 14.1% for o-chloroaniline and 3.7% for aniline. The above-mentioned procedure was repeated 10 times, and all the reaction mixtures thus obtained were mixed together. Subsequently, by use of a vibration type countercurrent liquid-liquid extraction apparatus having an inside diameter of 15 mm and an effective height of 2.0 m, extraction was carried out using n-butanol in an amount of 2 kg per kg of the combined reaction mixture. The extraction percentage of o-phenylenediamine was 98%. Subsequently, the raffinate aqueous solution was transferred to a flask and distilled. The resulting distillate separated into two layers. The aqueous layer was returned to the flask and only the organic layer was removed. After the distillate had come to be composed of an aqueous layer alone, 100 ml of water was dropped into the flask, and 100 ml water was freshly distilled off. Subsequently, 700 ml of a 25% by weight aqueous sodium hydroxide solution was dropped into the flask from its upper part under reflux. At this time, ammonia gas was generated. The contents became a black suspension. The reflux was continued for another 15 minutes and the suspension was then allowed to stand, upon which copper compounds comprising black cupric oxide as the main constituent precipitated. A small amount of the transparent supernatant was taken out and the concentration of copper dissolved therein was measured. It was 50 ppm. The suspension has a pH of 12.0. The flask was again heated, and air was blown into its contents for 1 hour while the contents were refluxed. The flask was allowed to stand, and the contents were filtered to recover the copper compounds comprising cupric oxide as the main constituent. The recovery was about 100% based on the calculated metallic copper content. The filtration was easy. A part of the filtrate was taken and the concentration of copper dissolved therein was measured. It was 6 ppm. The copper compounds recovered were again washed with distilled water and dried. In an Erlemmeyer flask were placed 7.0 g of the copper compounds dried, and 64.3 g of a 5% by weight aqueous hydrochloric acid solution (corresponding to 1 mole of hydrochloric acid per gram-atom of copper in the copper compounds) was added thereto, after which the resulting mixture was stirred for 10 minutes, thereafter heated to 50° C., and then stirred for 30 minutes to obtain a gray suspension of cupric chloride. The suspension was transferred to the aforesaid autoclave, and 150 g of o-dichlorobenzene, 225 g of water and 150 g of ammonia were further charged thereinto, after which the resulting mixture was subjected to reaction at 220° C. for 8 hours. There were obtained the following reaction results which were nearly equal to those obtained for the original cupric chloride dihydrate: The conversion was 95%, and the selectivities were 78% for o-phenylenediamine, 15% for o-chloroaniline and 4% for aniline.

COMPARATIVE EXAMPLE 1

The pH of 1 kg of the reaction mixture obtained in Example 1 was adjusted to 12.5 by adding thereto dropwise a 25% by weight aqueous sodium hydroxide solution while maintaining said reaction mixture at 60° C., to precipitate copper compounds. The precipitate was colloidal. The reaction mixture containing the precipitate was subjected to azeotropic distillation to recover o-dichlorobenzene, o-chloroaniline, chlorobenzene and aniline. In carrying out the azeotropic distillation, water was added so that the o-phenylenediamine concentration in said reaction mixture was kept in a range of 5 to 20% by weight.

By use of a vibration type countercurrent liquid-liquid extraction apparatus having an inside diameter of 15 mm and an effective height of 2.0 m, the o-phenylenediamine in the residue after the above-mentioned azeotropic distillation was extracted with 2 kg of tetrahydrofurane. In the raffinate aqueous solution, the aforesaid copper compounds precipitated were present in a colloidal condition. The copper compounds in the raffinate aqueous solution were separated by suction filtration to be recovered with 95% recovery in terms of metallic copper, but the suction filtration required a long time. The concentration of copper dissolved in the filtrate was determined to be 300 ppm.

EXAMPLE 3

Into a 1-liter, stainless steel autoclave equipped with an electromagnetic rotary stirrer were charged 150 g of o-dichlorobenzene, 375 g of 40% by weight aqueous ammonia and 8.6 g of cupric hydroxide, and they were heated to 220° C., and then subjected to reaction for 12 hours. After the reaction, the autoclave was cooled to 60° C., and the valve was gradually opened while stirring the contents, to release the excessive ammonia gas. The internal pressure was lowered to atmospheric pressure, after which the reaction mixture in the autoclave was transferred to another vessel and stored. The conversion was 95.3%, and the selectivities were 79% for o-phenylenediamine, 14.5% for o-chloroaniline and 3.8% for aniline. The above-mentioned reaction procedure was repeated 10 times, and all the reaction mixtures thus obtained were mixed together. Subsequently, by use of a vibration type countercurrent liquid-liquid extraction apparatus having an inside diameter of 15 mm and an effective height of 2.0 m, extraction was carried out using n-butanol in an amount of 2 kg per kg of the combined reaction mixture. The extraction percentage of o-phenylenediamine was 98%. Subsequently, the raffinate aqueous solution was transferred to a flask and distilled. The distillate separated into two layers. The aqueous layer was returned to the flask and only the organic layer was removed. After the distillate had come to be composed of an aqueous layer alone, 100 ml of water was dropped into the flask, and 100 ml of water was freshly distilled off.

Subsequently, the contents of the flask were adjusted to pH 10 by adding thereto 3.2 kg of a 25% by weight aqueous sodium hydroxide solution from its upper part under reflux. Ammonia gas was generated, and the contents changed in color to blue. Further, the contents of the flask were refluxed, and 0.1 kg of a 25% by weight aqueous sodium hydroxide solution was again added thereto while blowing air into the contents, to maintain the contents at pH 10. When air was blown thereinto for 1 hour, the contents became a light-blue suspension containing copper hydroxides. The flask was allowed to stand, and the contents were filtered to recover copper compounds comprising cupric hydroxide as the main constituent. The recovery was about 100% based on the calculated metallic copper content. The filtration was easy. A part of the filtrate was taken and the concentration of copper dissolved therein was measured. It was 10 ppm.

The copper compounds recovered were again washed with distilled water and dried. When 8.6 g of the dried copper compounds was taken, and 150 g of o-dichlorobenzene and 375 g of 40% by weight aqueous ammonia were added thereto, after which the resulting mixture was subjected to reaction at 220° C. for 13 hours in the aforesaid autoclave, to obtain the following reaction results which were nearly equal to those obtained for the original cupric hydroxide: The conversion was 95.4%, and the selectivities were 79% for o-phenylenediamine, 14% for o-chloroaniline and 4% for aniline.

COMPARATIVE EXAMPLE 2

The pH of 1 kg of the reaction mixture obtained in Example 3 was adjusted to 12.5 by adding thereto dropwise a 25% by weight aqueous sodium hydroxide solution while maintaining said reaction mixture at 60° C., to precipitate copper compounds. The resulting precipitate was colloidal. The reaction mixture containing the precipitate was subjected to azeotropic distillation to recover o-dichlorobenzene, o-chloroaniline, chlorobenzene and aniline. In carrying out the azeotrpic distillation, water was added so that the o-phenylenediamine concentration in said reaction mixture was kept in a range of 5 to 20% by weight.

By use of a vibration type countercurrent liquid-liquid extraction apparatus having an inside diameter of 15 mm and an effective height of 2.0 m, the o-phenylenediamine in the residue after the above-mentioned azeotropic distillation was extracted with 1 kg of n-butanol. In the raffinate aqueous solution, the aforesaid copper compounds precipitated were present in a colloidal condition. The copper compounds in the raffinate aqueous solution were separated by suction filtration to be recovered with 95% recovery in terms of metallic copper, but the suction filtration required a long time. The concentration of copper dissolved in the filtrate was determined to be 300 ppm.

EXAMPLE 4

Into a 1-liter, stainless steel autoclave equipped with an electromagnetic rotary stirrer were charged 150 g of p-dichlorobenzene, 375 g of 40% by weight aqueous ammonia and 7 g of cupric oxide, and they were heated to 220° C., and subjected to reaction for 6 hours. After the reaction, the autoclave was cooled to 60° C., and the valve was gradually opened while stirring the contents, to release the excessive ammonia gas. The internal pressure was lowered to atmospheric pressure, after which the reaction mixture in the autoclave was transferred to another vessel and stored. The conversion was 99.7%, and the selectivities were 92.3% for p-phenylenediamine, 4.8% for p-chloroaniline and 0.9% for aniline. The above-mentioned reaction procedure was repeated 10 times, and all the reaction mixtures obtained were mixed together, and subsequently, by use of a vibration type countercurrent liquid-liquid extraction apparatus having an inside diameter of 15 mm and an effective height of 2.0 m, extraction was carried out using tetrahydrofuran in an amount of 1.5 kg per kg of the combined reaction mixture. The extraction percentage of p-phenylenediamine was 98%. Subsequently, the residual aqueous solution after extraction was transferred to a flask and distilled to remove the tetrahydrofuran.

Subsequently, a detector of a pH meter was attached inside the flask, after which 100 g of calcium hydroxide and 100 ml of water were put therein. The flask was heated so that the temperature inside the flask became 90° to 95° C. Subsequently, a nitrogen gas was bubbled into the contents. When the bubbling was continued for some time while the temperature of the contents was maintained at 90° to 100° C., the pH of the contents lowered gradually and reached a constant value. Subsequently, the pH was raised by further adding a small amount of a 20% by weight suspension of calcium hydroxide, and bubbling was conducted until the pH became constant again. Thereafter, this procedure was repeated several times, and the addition of calcium hydroxide was stopped at the time when the pH of the contents became 6.2 finally. At this time, the contents were a light-blue suspension. After the bubbling was continued for another 10 minutes, the flask was allowed to stand, and the resulting precipitate of copper compounds was separated by filtration and recovered. When the recovery was calculated, assuming that the precipitate obtained was cupric hydroxide, it was as excessive as 121%. This was thought to be because the precipitate was contaminated with calcium hydroxide. The filtration could easily be carried out in a short time. A part of the filtrate was taken and the concentration of the copper component was measured. It was 3.5 ppm.

The copper compounds recovered were washed with distilled water and then dried. In the above autoclave was placed 10.4 g of the copper compounds dried together with 150 g of p-dichlorobenzene and 375 g of 40% by weight aqueous ammonia, and they were subjected to reaction at a temperature of 220° C. for 6 hours. In this reaction, the conversion was 99.8%, and the selectivities were 95.1% for p-phenylenediamine, 2.2% for p-chloroaniline and 0.8% for aniline. From these results, it can be seen that the copper compounds recovered by the treatment of addition of calcium hydroxide has a higher catalytic activity than the original cupric oxide.

COMPARATIVE EXAMPLE 3

The pH of 1 kg of the reaction mixture obtained in Example 4 was adjusted to 12.5 by adding thereto dropwise a 25% by weight aqueous sodium hydroxide solution while maintaining said reaction mixture at 60° C., to precipitate copper compounds. The precipitate was colloidal. The reaction mixture containing the precipitate was subjected to azeotropic distillation to recover p-dichlorobenzene, p-chloroaniline and aniline. In carrying out the azeotropic distillation, water was added so that the p-phenylenediamine concentration in said reaction mixture was kept in a range of 5 to 20% by weight.

By use of a vibration type countercurrent liquid-liquid extraction apparatus having an inside diameter of 15 mm and an effective height of 2.0 m, the p-phenylenediamine in the residue after the above-mentioned azeotropic distillation was extracted with 2 kg of n-butanol. In the raffinate aqueous solution, the aforesaid copper compounds precipitated were present in a colloidal condition. The copper compounds in the raffinate aqueous solution were separated by suction filtration to be recovered with 95% recovery in terms of copper, but the suction filtration required a long time. The concentration of copper in the filtrate was determined to be 300 ppm.

EXAMPLE 5

Into a 3-liter, stainless steel autoclave equipped with an electromagnetic rotary stirrer were charged 450 g of p-dichlorobenzene, 1,125 g of 40% by weight aqueous ammonia and 21 g of cupric oxide, and they were heated to 210° C., and then subjected to reaction for 5 hours. After the reaction, the autoclave was cooled to 60° C., and the valve was gradually opened while stirring the contents, to release the excessive ammonia gas. The internal pressure of the autoclave was lowered to a pressure near atmospheric pressure, after which a part of the reaction mixture was taken and then analyzed to find that the conversion was 99.8%, and the selectivities were 92.0% for p-phenylenediamine, 4.0% for p-chloroaniline and 0.8% for aniline. In the reaction mixture, 312 g (5.83 moles) of ammonium chloride had been generated. Thereafter, the autoclave was allowed to stand until its temperature lowered to room temperature. Subsequently, 326 g of an aqueous solution containing 163 g (4.08 moles) of sodium hydroxide was charged into the autoclave with stirring. Thereafter, the autoclave was again heated to 60° C., and its contents were transferred to another vessel and stored. The above procedure was repeated 5 times, and all the reaction mixtures obtained by the 5 repetitions were mixed together. Subsequently, by use of a vibration type counter-current liquid-liquid extraction apparatus having an inside diameter of 15 mm and an effective height of 2.0 m, extraction was carried out by supplying tetrahydrofuran in an amount of 1 kg per kg of the combined reaction mixture. The extraction percentage was 99.5%. Two liters of the raffinate aqueous solution after extraction was transferred to a 3-liter flask and distilled at atmospheric pressure to remove the tetrahydrofuran.

Subsequently, a detector of a pH meter was attached inside the flask, and a needle for introducing gas which was connected to a nitrogen-feeding line was set inside the flask. Further, the flask was equipped with a dropping funnel containing a 30% by weight sodium hydroxide solution. The flask was again heated, and when brought into a refluxed condition, its contents were adjusted to pH 12.5 by addition of about 65 ml of an aqueous sodium hydroxide solution. At this time, ammonia gas was generated and at the same time, black cupric oxide was precipitated. Thereupon, the nitrogen-feeding line was opened, and bubbling was continued for about 30 minutes while controlling the temperature of the contents so as to be 90° C., after which the flask was allowed to stand. About 7 liters of the raffinate aqueous solution was treated by repeating the above-mentioned procedure for treating the raffinate aqueous solution. The raffinate aqueous solution treated was filtered to recover 104.0 g of cupric oxide. The filtration was easy. A part of the filtrate was taken and the concentration of copper dissolved therein was measured. It was 6 ppm.

What is claimed is:

1. A process for producing an aromatic amine from an aromatic halide and ammonia, characterized by comprising the following steps (1), (2) and (3):
   step (1): reacting the aromatic halide with ammonia in the presence of water using a catalyst comprising a copper compound as the main constituent,
   step (2): extracting the aromatic amine from the reaction mixture obtained in step (1) without depositing and separating the copper component contained in the reaction mixture, and
   step (b 3): depositing copper compounds by addition of an alkali metal hydroxide and/or an alkaline earth metal hydroxide to the raffinate aqueous solution which is obtained in step (2), and separating the same.

2. A process according to claim 1, wherein the aromatic halide is at least one member selected from the group consisting of chlorobenzene, dichlorobenzene, trichlorobenzene, chloroaniline, dichloroaniline, chloronitrobenzene and dichloronitrobenzene.

3. A process according to claim 2, wherein the amount of the ammonia used is 2 to 25 moles per gram-atom of the halogen of the aromatic halide which requires amination.

4. A process according to claim 3, wherein the amount of the water used is 30 to 70% by weight based on the total weight of the ammonia and the water.

5. A process according to claim 4, wherein the amount of the copper compound used is 0.01 to 0.4 gram-atom in terms of copper atom per mole of the aromatic halide.

6. A process according to claim 5, wherein the copper compound is a copper oxide, a copper hydroxide or a copper halide.

7. A process according to claim 6, wherein the reaction is effected at 170° to 250° C.

8. A process according to claim 7, wherein the extraction is carried out using an extracting solvent comprising as the main constituent an aliphatic alcohol whose main chain has 3 to 6 carbon atoms, aniline, an aniline derivative or tetrahydrofuran.

9. A process according to claim 1, wherein the extraction is carried out using an extracting solvent comprising tetrahydrofuran as the main constituent.

10. A process according to claim 8, wherein the alkali metal hydroxide in step (3) is sodium hydroxide or potassium hydroxide, and the alkaline earth metal hydroxide is magnesium hydroxide or calcium hydroxide.

11. A process according to claim 1, wherein before step (2), an alkali metal hydroxide and/or an alkaline earth metal hydroxide is added to the reaction mixture obtained in step (1) in an amount of 0.05 to 1 gram-equivalent per gram-ion of halogen ions contained in said mixture.

12. A process according to claim 11, wherein the alkali metal hydroxide is sodium hydroxide or potassium hydroxide, and the alkaline earth metal hydroxide is calcium hydroxide or magnesium hydroxide.

13. A process according to claim 1, 9 or 11, wherein the copper compounds separated in step (3) is used again in step (1).

14. A process according to claim 1 or 11, wherein the aromatic halide is dichlorobenzene and the aromatic amine is phenylenediamine.

* * * * *